(12) United States Patent
Palangi et al.

(10) Patent No.: US 10,613,081 B2
(45) Date of Patent: Apr. 7, 2020

(54) QUALITY CONTROL SYSTEM AND KIT FOR AUTOMATED ELISA DEVICES

(71) Applicants: Alireza Palangi, Tehran (IR); Samira Bayat Bidkorpeh, Tehran (IR)

(72) Inventors: Alireza Palangi, Tehran (IR); Samira Bayat Bidkorpeh, Tehran (IR)

(*) Notice: Subject to any disclaimer, the term of this patent is extended or adjusted under 35 U.S.C. 154(b) by 0 days.

(21) Appl. No.: 15/821,675

(22) Filed: Nov. 22, 2017

(65) Prior Publication Data
US 2018/0095077 A1  Apr. 5, 2018

(51) Int. Cl.
*G01N 33/543* (2006.01)
*G01N 33/76* (2006.01)
*G01N 35/00* (2006.01)

(52) U.S. Cl.
CPC ..... *G01N 33/543* (2013.01); *G01N 33/54366* (2013.01); *G01N 33/76* (2013.01); *G01N 35/00594* (2013.01); *G01N 35/00623* (2013.01); *G01N 2035/00653* (2013.01); *G01N 2333/59* (2013.01)

(58) Field of Classification Search
CPC .......... G01N 33/543; G01N 33/54366; G01N 35/00594; G01N 35/00623; G01N 33/76
See application file for complete search history.

(56) References Cited

U.S. PATENT DOCUMENTS

| | | |
|---|---|---|
| 4,043,756 A | 8/1977 | Sommervold |
| 4,858,154 A | 8/1989 | Anderson et al. |
| 4,892,405 A | 1/1990 | Sorensen et al. |
| 5,157,455 A | 10/1992 | Macri et al. |
| 7,309,372 B2 | 12/2007 | Kahlbaugh et al. |
| 10,082,500 B2 | 9/2018 | Baudenbacher et al. |
| 2008/0311602 A1 | 12/2008 | Wang et al. |
| 2009/0252749 A1* | 10/2009 | Leister ............ C07K 14/70521 424/178.1 |
| 2011/0294145 A1* | 12/2011 | Victor ................ C07K 16/18 435/7.92 |

* cited by examiner

*Primary Examiner* — Melanie Brown
(74) *Attorney, Agent, or Firm* — NovoTechIP International PLLC

(57) ABSTRACT

A kit and method for evaluation of the quality and the operating parameters of any types of fully automated open ELISA instruments are disclosed. The kit and method can be used to reliably assess quality control parameters including precision, volume removal accuracy, plate reader accuracy, plate reader linearity, plate washer quality, drift absence, and carryover absence. The evaluation can be completed in a timely and cost-effective manner and provide laboratories with the ability to readily validate the operation and performance of a fully automated ELISA instrument.

19 Claims, 16 Drawing Sheets

$$\bar{x} = \frac{\sum_{i=1}^{n} x_i}{n}$$

FIG. 6A

$$SD = \sqrt{\frac{\sum (x - \bar{x})^2}{n}}$$

FIG. 6B

$$CV = \frac{s}{\bar{x}} \times 100$$

FIG. 6C

QUALITY CONTROL SYSTEM AND KIT FOR AUTOMATED ELISA DEVICES

CROSS-REFERENCE TO RELATED APPLICATION

This application claims the benefit of priority from Iran Patent Application Serial No 139550140003010755, filed on Nov. 27, 2016 and entitled "FULLY AUTOMATED OPEN ELISA PROCESSOR QUALITY CONTROL KIT," which is incorporated herein by reference in its entirety.

BACKGROUND

The Enzyme Linked ImmunoSorbent Assay, or ELISA, is a test used for detecting and quantifying antibodies or antigens. This technique is used in immunology, microbiology, endocrinology, and other fields, as well as in the food industry. The ELISA can measure the concentration of antibodies or antigens (generally referred to as analyte) in a solution by the observation of a color change.

Generally, an antigen is any molecule that induces the production of antibodies when introduced into an organism. For example, any foreign particle such as portions of bacteria, viruses, pollen, and other such molecules as well as self-antigens can be identified by an organism as antigens. In addition, antibodies are proteins produced by the immune system in response to antigen detection.

The ELISA process involves a coating or binding of an antigen, antibody, or other molecule to a solid support as a membrane or a 96-well micro plate or microtiter plate, also referred to as an ELISA plate. An enzyme conjugate is used to detect the binding of an antigen or an antibody to solid phase attached molecule. The enzyme converts a colorless substrate (chromogen) to a colored product, thereby indicating the presence of antigen: antibody binding. Thus, the ELISA test can be used to detect either the presence of antigens or antibodies in a sample depending on how the system is set up.

To run an ELISA test—by hand or automated instruments—plate washer instruments, plate reader instruments, and fully automated ELISA instruments are globally manufactured and distributed worldwide. According to the International Organization for Standardization's standard providing general requirements for the competence of testing in medical laboratories, including ISO 15189, as well as national standards across many countries. Validation of instrument quality is crucial. Thus, quality control processes for such quality validation are also important and necessary for components such as plate washer instruments, plate reader instruments, and fully automated ELISA instruments.

The lack of a comprehensive tool to assess the quality control parameters of fully automated ELISA instruments has resulted in the reliance of diagnostic clinical laboratories solely on commercial serum controls that are available in the market in order to assess the experimental results of such instruments. However, these commercial serum controls are associated with many drawbacks. For example, it is known that use of the serum controls permit only the assessment of quality parameters such as precision and accuracy, while other important quality parameters involved in the use of a fully automated EISA instrument cannot be evaluated. Furthermore, when errors arise in the results obtained from commercial serum controls, there is no debugging mechanism to indicate that the problem stems from the ELISA kit that is being used rather than from the fully automated ELISA instrument. In addition, commercial serum controls are not available for all target analytes. As each commercial control serum contains a limited category of target analytes, to assess the quality of all the target analytes tests, a number of commercial serum control must be used. Furthermore, due to a broad range of acceptable results suggested by commercial serum control manufacturers, the underlying problems in an instrument may not be immediately captured, especially during the initial instrument setup. These commercial serum controls are also expensive and extended use of these materials is not cost-effective.

Thus, as various processes and techniques across a wide variety of medical and diagnostic clinical fields have become increasingly automated, the need for an efficient and effective means of providing reliable quality control for such systems has become increasingly paramount. Currently, there are some protocols and kits available to assess the quality of plate washer instruments and plate reader instruments used in manually operated ELISA tests. However, there remains a need for protocols, kits, and/or equipment to assess the quality of fully automated ELISA instruments.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

In one general aspect, the present disclosure is directed to a kit and method for evaluating quality control parameters of an automated ELISA instrument. The method includes preparing a micro plate that includes a plurality of plate wells, adding a sample to at least one plate well of the micro plate, and adding a first amount of conjugated enzyme to the at least one plate well to obtain a first mixture. The method also includes washing the first mixture with a wash buffer, preparing and adding a second amount of substrate solution to the first mixture to obtain a second mixture, preparing and adding a third amount of stop solution, and obtaining a reading from the automated ELISA instrument. In addition, the method includes obtaining a first reading from plate wells 1 to 16 of the automated ELISA instrument and calculating a first mean for the data of the first reading. The method further includes comparing the first mean with a first acceptable range provided in a certificate of analysis (COA) paper for plate wells 1 to 16, thereby determining whether readings and volume removal for the automated ELISA instrument are accurate.

The above general aspect may include one or more of the following features. In some implementations, the step of preparing the micro plate includes pre-coating a bottom surface of the plate wells with anti-Human Thyroid Stimulating Hormone (TSH) antibody. In other implementations, the method also includes drying the plate wells. As one example, the step of preparing the substrate solution can further includes adding 5 µL $H_2O_2$ and 10 µL tetra-methylbenzidine (TMB) to 100 mL acetate buffer. In another example, the step of preparing the stop solution also includes adding 1 mL tartrazine to 11 mL sulfuric acid (1 M). In some cases, the micro plate includes at least 96 plate wells. In another implementation, the method may include adding 50 µL of a first solution to plate wells 1 to 16, adding 50 µL of a second solution to plate wells 17 to 32, adding 50 µL of a third solution to plate wells 33 to 48, adding 50 μL of a fourth solution to plate wells 49 to 64, adding 50 μL of a fifth solution to plate wells 65 to 80, and adding 50 μL of the first solution to plate wells 81 to 96. In another case, the method can include preparing the first solution by dissolving approximately 20 mg TSH powder in approximately 5 mL delipidated serum. In other cases, the method can also include preparing the second solution by dissolving approximately 13 mg TSH powder in approximately 5 mL dilapidated serum, and preparing the third solution by dissolving approximately 28 mg TSH powder in approximately 5 mL dilapidated serum. In some implementations, the step of adding conjugated enzyme to the at least one plate well includes adding 50 μL of horseradish peroxidase (HRP) to the at least one plate well.

Furthermore, the above general aspect may include one or more of the following features. For example, the method can also include obtaining a second reading from plate wells 17 to 32 of the automated ELISA instrument, calculating a second mean for data of the second reading, and comparing the second mean with a second acceptable mean range provided in the COA paper for plate wells 17 to 32, thereby determining whether readings and volume removal for the automated ELISA instrument are accurate. In some implementations, the method includes obtaining a third reading from plate wells 33 to 48 of the automated ELISA instrument, calculating a third mean for data of the third reading, and comparing the third mean with a third acceptable mean range provided in the COA paper for plate wells 33 to 48, thereby determining whether readings and volume removal for the automated ELISA instrument are accurate. In another implementation, the method further includes obtaining a fourth reading from plate wells 49 to 64 of the automated ELISA instrument, calculating a fourth mean for data of the fourth reading, and comparing the fourth mean with a fourth acceptable mean range provided in the COA paper for plate wells 49 to 64, thereby determining whether a plate washer of the automated ELISA instrument is functioning within normal operating parameters. As another example, the method can include obtaining a fifth reading from plate wells 65 to 80 of the automated ELISA instrument, calculating a fifth mean for data of the fifth reading, and comparing the fifth mean with a fifth acceptable mean range provided in the COA paper for plate wells 65 to 80, thereby determining whether readings and volume removal for the automated ELISA instrument are accurate. In some cases, the method also includes obtaining a sixth reading from plate wells 81 to 96 of the automated ELISA instrument, calculating a sixth mean for data of the sixth reading, and comparing the sixth mean with a sixth acceptable mean range provided in the COA paper for plate wells 81 to 96, thereby determining whether there is drift in the automated ELISA instrument. In one implementation, the method may include calculating a first coefficient of variation (CV) for data of the first reading, and comparing the first coefficient of variation with a first acceptable CV range provided in the COA paper for plate wells 1 to 16, thereby determining a precision of the automated ELISA instrument. In one example, the precision of the automated ELISA instrument is unsuitable if the first coefficient of variation is greater than 9.7%. In another example, the method includes comparing the second mean with a second acceptable range provided in the COA paper for plate wells 17 to 32, thereby determining whether there is carryover in the automated ELISA instrument. In some implementations, the method includes obtaining a second reading from plate wells 17 to 32, a third reading from plate wells 33-48, a fourth reading from plate wells 49-64, a fifth reading from plate wells 65 to 80, and a sixth reading from plate wells 81-96, calculating a second mean for the data of the second reading, calculating a third mean for the data of the third reading, calculating a fourth mean for the data of the fourth reading, calculating a fifth mean for the data of the fifth reading, and calculating a sixth mean for the data of the sixth reading, comparing the second mean with a second acceptable mean range provided in the COA paper for plate wells 17 to 32, and determining there is carryover in the automated ELISA instrument if the second mean is higher than the second acceptable mean range and each of the readings for plate wells 33 to 96 approach values provided in the COA paper. In addition, in another implementation, the method can include obtaining a second reading from plate wells 81 to 96, calculating a second mean for the data of the second reading, and determining there is drift in the automated ELISA instrument if the second mean is more than 10% of the first mean Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the following claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 6A is an equation for determining the mean of a data set;

FIG. 6B is an equation for determining the standard deviation of a data set;

FIG. 6C is an equation for determining the coefficient of variation for a data set;

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

As discussed above, there is currently a need in diagnostic clinical laboratories for a kit or a method to facilitate the validation of the quality of operation of fully automated ELISA instruments. The disclosed method can offer an opportunity to ascertain the accuracy of an ELISA instrument either at the time of purchase, or during the application of the instrument in paraclinical centers, clinics, and hospitals.

The following description provides various implementations of a kit and a method of providing quality control for automated ELISA systems. As described above, the ELISA laboratory technique involves either marking an antigen or antibody with an enzyme. The enzyme, in the presence of its substrate, can send a signal by developing a change in color during the chemical reaction, and such a change can be measured, and correspond to a presence or quantity of analytes. ELISA protocols and systems have developed over the years, and can now be operated in different formats. Two such formats include Direct ELISA and Indirect ELISA. In Direct ELISA, a labeled primary antibody is used that reacts directly with the antigen. In Indirect ELISA, an unlabeled primary antibody is used in conjunction with a labeled secondary antibody that has specificity for the primary antibody.

Figure 1:
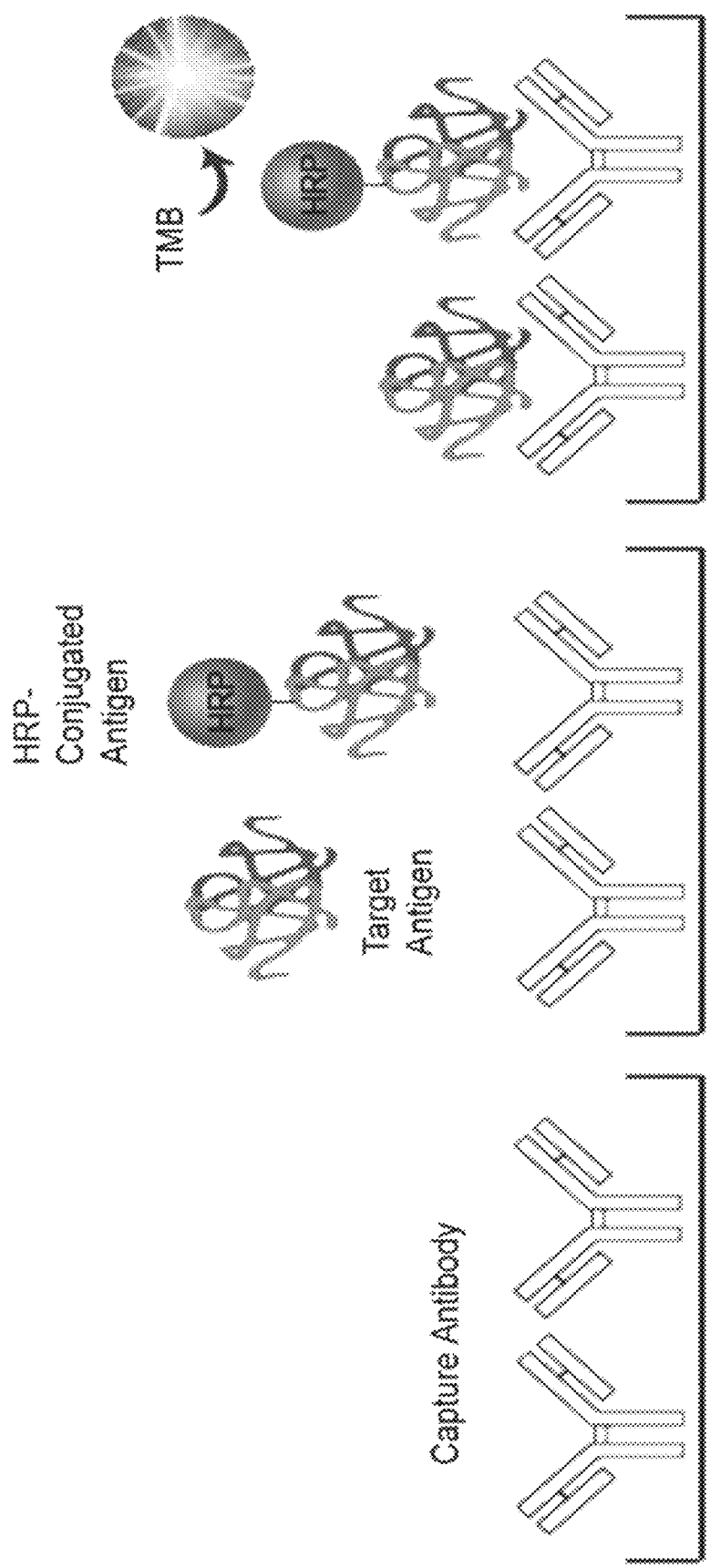
FIG. 1 is a schematic representation of an ELISA testing in a competitive format.

In addition, other more sensitive ELISA formats are being utilized, including Competitive ELISA and Sandwich ELISA. In Competitive ELISA testing, represented schematically by LifeSpan Biosciences, Inc., for purposes of reference in FIG. 1, a sample and a marked antigen are simultaneously added to ELISA plate wells (pre-coated with anti-antigen antibodies), and the available antigen in the sample competes with the marked antigen in binding to a specific antibody over the plate surface. In the example of FIG. 1, the marked antigen is a Horseradish peroxidase (HRP)-conjugated antigen, though it should be understood that in other cases, other enzymes can be used. Following removal of the unbound marked antigen by washing of the plate wells, an enzyme substrate is added. In FIG. 1, the substrate is 3,3',5,5'-Tetramethylbenzidine or TMB, which is a chromogenic substrate used in staining procedures. However, in other cases, another substrate can be used. The substrate changes in color in the presence of the marked antigen (enzyme), which is measurable. If the concentration of antigen in the sample is low, a higher number of marked antigens reacted with the antibody. As such, an inverse relationship exists between the immunosorbent detection and antigen concentration in the sample.

Figure 2:
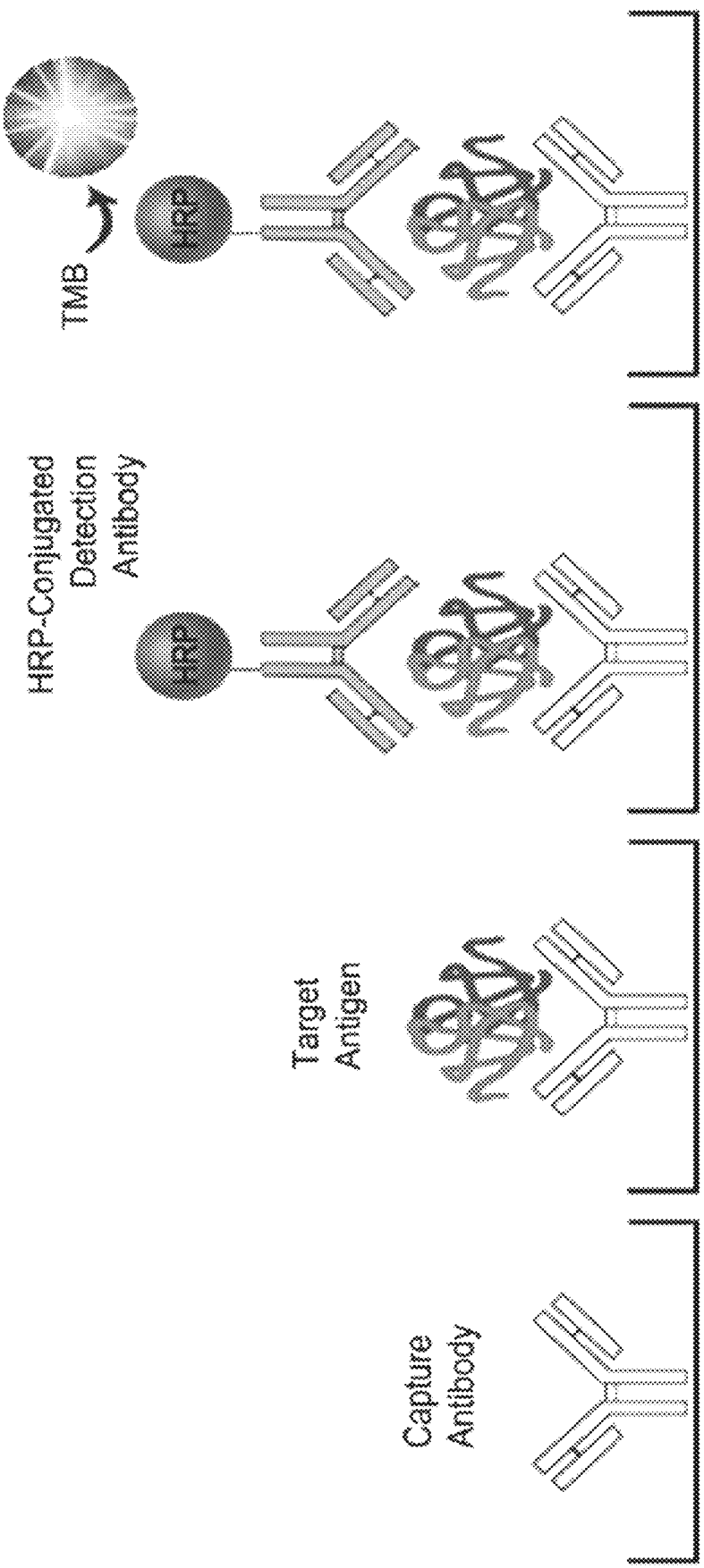
FIG. 2 is a schematic representation of an ELISA testing in a sandwich format.

In the Sandwich ELISA, represented schematically by LifeSpan Biosciences, Inc., for purposes of reference in FIG. 2, a molecular "sandwich" is formed that permits measurement of the amount of antigen trapped between two layers of antibodies. The primary antibody, or the 'capture' antibody, is bound to a solid surface (such as an ELISA plate well). A sample with an antigen is then added and binds to the primary antibody. A detection antibody, which is also called a conjugated or secondary antibody, binds to an enzyme. In the example shown in FIG. 2, the detection antibody is a Horseradish peroxidase (HRP)-conjugated antibody, though it should be understood that in other cases, other enzymes can be used. The secondary antibody links to the other side of the antigen, thereby sandwiching the antigen between the two antibodies. After removal of any non-bound secondary antibody, an enzyme substrate is added that changes in color during the chemical reactions. In FIG. 2, the substrate is TMB. However, in other cases, another substrate can be used. Thus, in this format, in contrast to the competitive format, a direct relationship exists between immunosorbent detection and antigen concentration in the sample.

The Competitive and Sandwich ELISA techniques can be run either manually or by use of an automated system. When operated manually, the steps involving addition of different samples and solutions are performed by a user. However, the steps involving washing can be performed either by a user or by a plate washer instrument. In addition, the steps involving the final reading can also be performed by a plate reader instrument. In contrast, in a fully automated ELISA instrument, all steps involving the adding of different samples and solutions, washing, and reading, are performed automatically. In the automated method and system, a user merely sets up the order and the removal volume of different samples and solutions, the number and the conditions of the washing step, and the wavelength of the reading step in the instrument.

Thus, it may be understood that the quality control process for a manually operated ELISA and for an automated ELISA can differ in many respects. In some implementations, in order to perform a quality assessment of a fully automated ELISA instrument, parameters such as (1) precision, (2) volume removal accuracy, (3) plate reader accuracy, (4) plate reader linearity, (5) plate washer quality, (6) absence of drift, and/or (7) absence of carryover should be evaluated. Each of these parameters can affect the performance and results of a fully automated ELISA, and can be highly important to quality control. More details with respect to these parameters are provided below.

Generally, with respect to ELISA instrumentation, acceptable precision refers to satisfactory replication of data obtained from different experimental runs on a sample. In addition, volume removal accuracy refers to sufficient proximity between the volume removal by an instrument and the actual defined volume. Similarly, plate reader accuracy refers to sufficient proximity between the optical density read by the instrument identifier and the actual optical density. In addition, plate reader linearity refers to accurate reading in various values of optical density. Plate washer quality refers to the accurate washing of plate wells by an instrument. The absence of drift refers to result similarity from the beginning to the end of an experiment. Finally, the absence of carryover refers to the absence of effects of the results of different samples on one another.

Therefore, it can be understood that defects or problems in any of the above-mentioned quality control parameters may result in a variety of quality issues in the use of the ELISA instrumentation. For example, different results may be obtained from different experimental runs on one sample due to a defect in instrument precision. Furthermore, obtained experimental results may be different from actual results due to problems in volume removal accuracy and/or plate reader accuracy. In addition, obtained experimental results for some sample concentrations may be different from actual results due to problems in plate reader linearity. Similarly, obtained experimental results may differ from actual results (generally higher than actual) as a consequence of problems in the plate washer process. The presence of drift can lead to experimental results from repeated runs showing an increasing or a decreasing spectrum effect in such a way that the difference from the actual results grows as the testing moves away from the beginning of the plate wells, towards the ending of the plate wells. Furthermore, experimental results from one sample may affect the next sample due to the presence of carryover.

Any problems with respect to one or more of the above identified quality control parameters of a fully automated ELISA instrument can have significant effects on the results of clinical tests. These effects can lead to inaccuracies and errors further down the chain—for example, in the screening, diagnosis, treatment monitoring, and other aspects of care for the large population of patients whose conditions require the measurement of various molecules, such as cancer, infectious diseases, infertility, hormonal imbalances, and other such conditions. As such, a means of reliably assessing these quality parameters becomes critical. In addressing this essential need, implementations of a new, comprehensive quality control kit for use with a fully automated ELISA instrument as a diagnostic tool in clinical laboratories are presented herein.

In order to introduce the reader to some implementations of the present disclosure, a brief overview of one example of a quality control kit for use with a fully automated ELISA system ("first kit") is provided herein. For purposes of this example, the first kit was applied to a sandwich-format ELISA configured to detect Thyroid Stimulating Hormone (TSH). A sample of TSH and anti-TSH conjugated detection antibody was added in a substantially simultaneously manner to a plate well, such that the TSH was sandwiched between a capture antibody bound to the bottom surface of one of the plate wells and the conjugated antibody during incubation. The unbound molecules were removed by washing of the plate well. Following the washing step, a substrate solution was added to the plate well. The effect of the enzyme-conjugated antibody on the substrate led to a change in color, such that the substrate developed a blue coloring. A stop solution was then added to the plate well, stopping the enzymatic reaction, and turning the solution to yellowish color in which the absorbance measured in approximately 450 nm wavelength with a reference filter of 630 nm wavelength.

Figure 3:
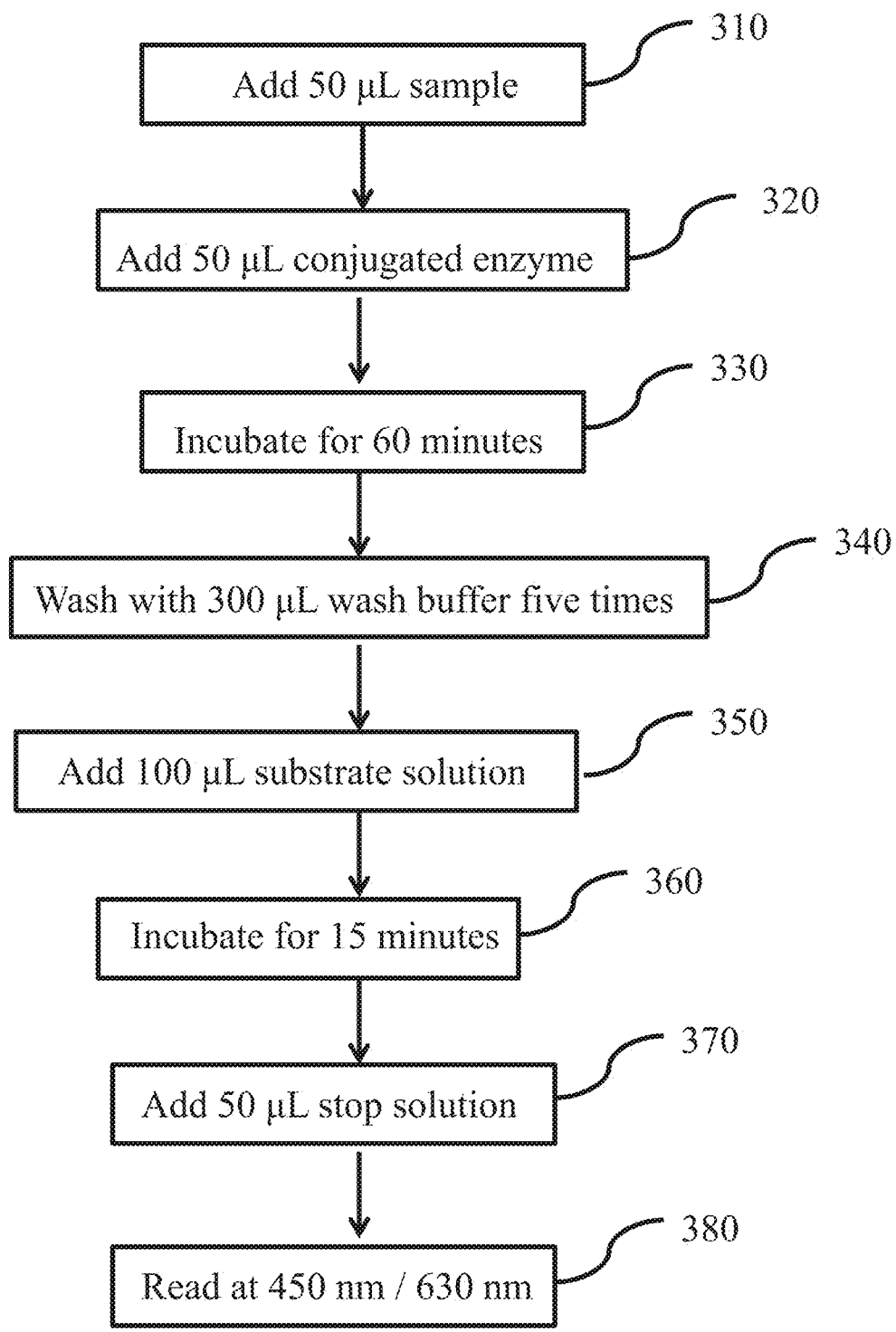
FIG. 3 is a flow chart illustrating an implementation of a method of collecting data for an ELISA instrument.

Referring to FIG. 3, a flow chart representing one implementation of the above-described first kit is depicted. In this implementation, the kit preparation includes a first step 310 of adding about 50 μL of a sample to a plate well in a micro plate, and adding about 50 μL of conjugated enzyme in a second step 320. The solution is incubated for approximately 60 minutes in a third step 330. Following the incubation step, the solution is washed five times with approximately 300 μL of wash buffer in a fourth step 340. A fifth step 350 includes adding 100 μL of substrate solution to the solution. The solution is then incubated for approximately 15 minutes in a sixth step 360. Another approximately 50 μL of stop solution is added to the solution in a seventh step 370, and a reading is obtained in an eighth step 380, in this case at a wavelength of 450 nm with a reference filter of 630 nm.

Figure 4:
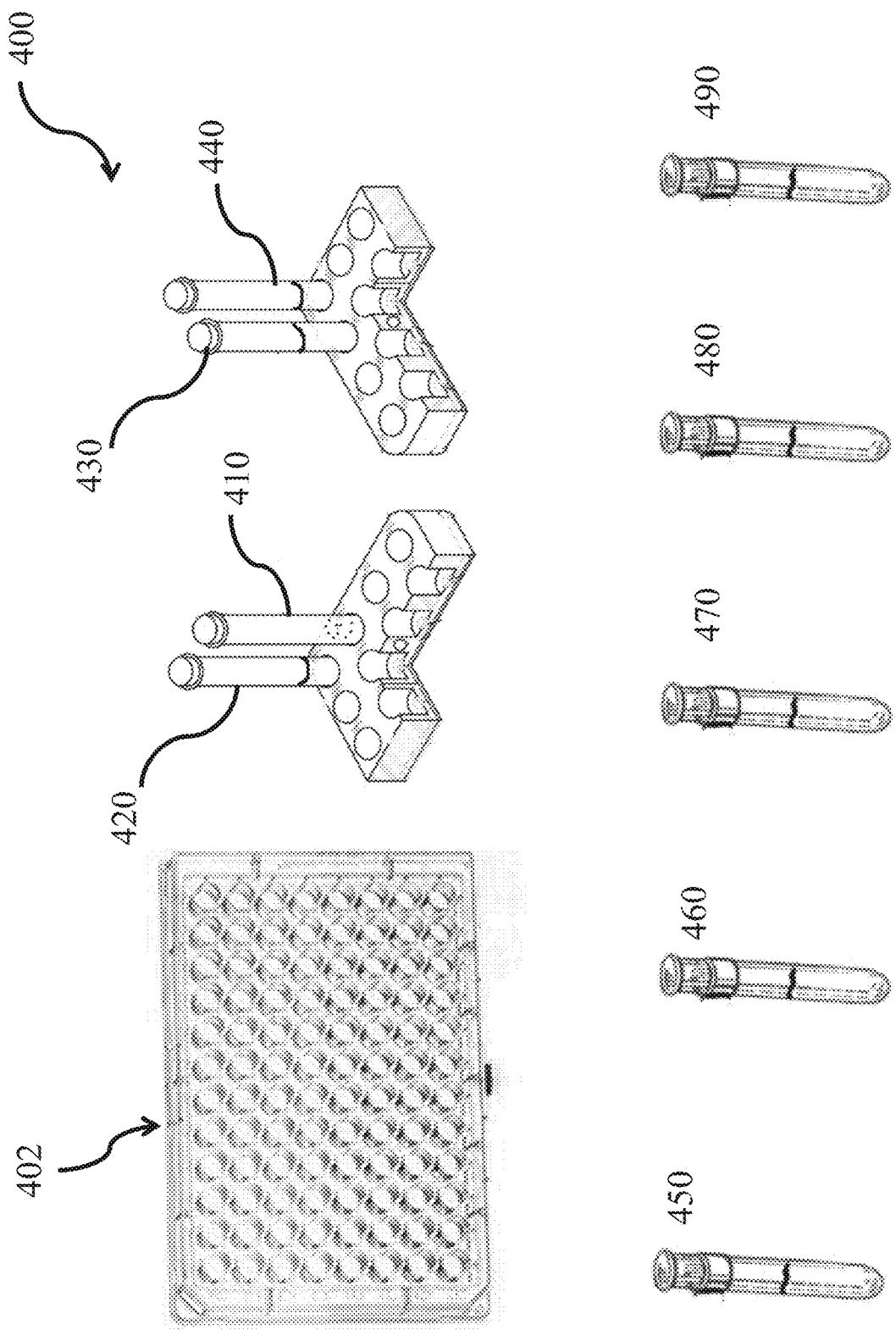
FIG. 4 depicts an implementation of a quality control kit for use with an ELISA instrument.

In order to provide a general overview of the kit to the reader, FIG. 4 presents some components or tools that may be included in an implementation of the quality control kit. In FIG. 4, it can be seen that a kit 400 can include (1) a 96-well plate pre-coated with anti-Human TSH antibody ("well plate") 402; (2) a conjugated enzyme 410, such as horseradish peroxidase (HRP) that is bound to the anti-Human TSH antibody; (3) a wash buffer 420; (4) a chromogene 430 or substrate solution; (5) and a stop solution 440. In one implementation, the stop solution includes a yellow dye reagent, though in other implementations, other buffers can be used.

In addition, in different implementations, the kit 400 includes a plurality of solutions. In this example, the kit 400 includes (6) a first solution ("Solution 1") 450, (7) a second solution ("Solution 2") 460, (8) a third solution ("Solution 3") 470, (9) a fourth solution ("Solution 4") 480, and (10) a fifth solution ("Solution 5") 490. In other implementations, a kit can include fewer or a greater number of solutions. Furthermore, in one implementation, Solution 1 contains about 20 units TSH in mL, Solution 2 contains about 13 units TSH in mL, Solution 3 contains about 28 units TSH in mL, Solution 4 is a concentrated yellow dye reagent, and Solution 5 is distilled water. In some implementations the proportion of each solution relative to other solutions can be significant. In other implementations, the solutions may vary in composition, amount, and/or concentration. In some implementations, the kit further includes (11) a Certificate of Analysis (COA) Paper, configured to provide acceptable ranges for test results.

EXAMPLE

In order to allow the reader to more readily appreciate the aspects of the elements identified above with respect to FIG. 4, details regarding one example implementation of the preparation and/or procurement of these elements are presented below. It should be understood that the steps below provide one methodology of preparing the various elements of the kit as an example only, and that other kits may include the same or similar elements that were prepared through alternative methods or sources that differ from those described below and include the same features as the kits of the present disclosure. In addition, the times, temperatures, sources, concentrations, and/or quantities identified below for each of the components may be approximate and can vary depending on the desired setup of the kit.

Figure 5:
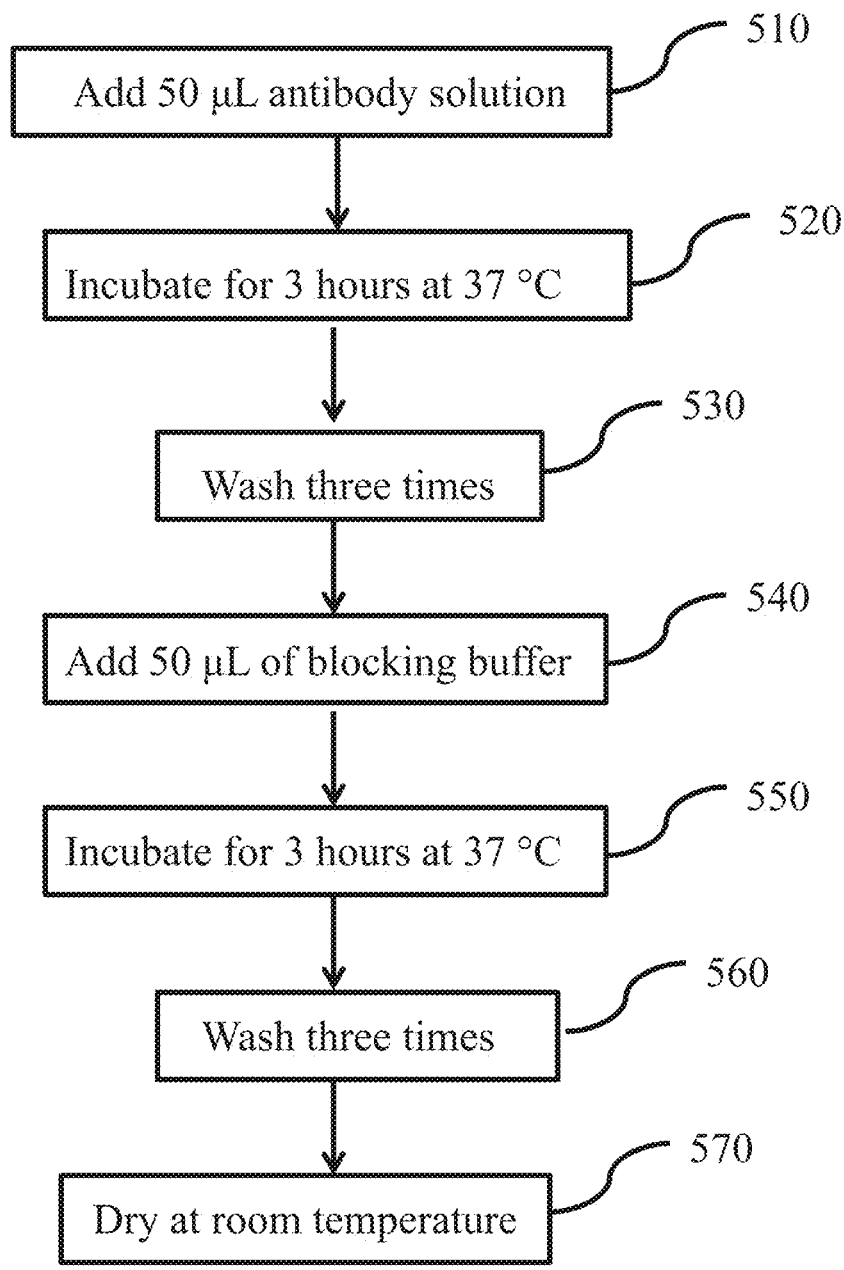
FIG. 5 is a flow chart illustrating an implementation of a method of preparing a plurality of plate wells in a microplate for use with the quality control kit of FIG. 4.

(1) Preparation of a 96-well Plate. A 96-well PVC plate was purchased from Orange manufacturing company. Referring to FIG. 5, the method includes a first step 510 pre-coating the bottom surface of the plate wells with anti-Human TSH antibody in which 50 μg anti-Human TSH antibody (purchased from Abcam company) was dissolved in 10 mL phosphate buffer solution (PBS, containing 15 mM of $Na_2HPO_4$ and 35 mM of $NaH_2PO_4$) at pH equal to 7.2. In addition, 50 μL of the prepared diluted sample was added to each plate well and incubated at 37° C. for three hours in a second step 520. Immediately following this step, the solutions were removed from each plate well, and the plate was washed three times with PBS as a third step 530. In order to block the remaining binding sites available on the bottom surface of the plate wells, about 50 µL of a blocking buffer (containing 0.1% casein in PBS) was then added to each plate well in a fourth step 540, and again the plate was incubated at 37° C. for three hours in a fifth step 550. Immediately following this step, the solutions were removed from each plate well, and the plate was washed again three times with PBS in a sixth step 560. In a seventh step 570, the wells were left at room temperature to dry overnight.

(2) Conjugated Enzyme. The conjugated enzyme in this example contains HRP bound to anti-Human TSH antibody, and was purchased as ready-to-use from the Dako company.

(3) Preparation of a Wash Buffer. A phosphate buffer solution at pH ranging between 7.2 to 7.4 was prepared as the concentrated wash buffer.

(4) Preparation of a Stop solution. The stop solution was prepared by adding 1 mL tartrazine to 11 mL sulfuric acid (1 M).

(5) Preparation of a Substrate Solution. The substrate was prepared by adding 5 µL $H_2O_2$ and 10 µL tetra-methylbenzidine (TMB) to 100 mL acetate buffer (sodium acetate, 0.1 M).

(6) Preparation of Solution 1. Solution 1 was prepared by dissolving 20 mg TSH powder (purchased from Sigma company) in 5 mL delipidated serum (purchased from the Merck company).

(7) Preparation of Solution 2. Solution 2 was prepared by dissolving 13 mg TSH powder (purchased from the Sigma company) in 5 mL delipidated serum (purchased from the Merck company).

(8) Preparation of Solution 3. Solution 3 was prepared by dissolving 28 mg TSH powder (purchased from the Sigma company) in 5 mL delipidated serum (purchased from the Merck company)

(9) Preparation of Solution 4. Solution 4 in this example is concentrated tartrazine and was purchased as ready-to-use from the Behavaran company.

(10) Preparation of Solution 5. Solution 5 constituted a quantity of distilled water.

(11) Certificate of Analysis (COA) Paper. For purposes of this example, a COA paper was obtained by running experiments on six different instruments over three consecutive days. The ranges were calculated by reading data value sets from each of plate wells 1 through 16. In this case, three data sets were read from a calibrated Dynex instrument, and the remaining three data sets were read from a calibrated Autoplex instrument. The mean, standard deviation, and coefficient of variation for each data set, which were read from plate wells 1 to 16, 17 to 32, 33 to 48, 49 to 64, 65 to 80, and 81 to 96, were calculated by respectively using Formulas 1, 2, and 3, presented in FIGS. 6A, 6B, and 6C. For purposes of reference, acceptable ranges for the test results calculated in this example produced a Mean Optical Density of plate wells as 1 to 16±3 SD. A similar method was also applied to the data sets read in other groups (plate wells 17 to 32, 33 to 48, 49 to 64, 65 to 80, and 81 to 96).

Figure 7:
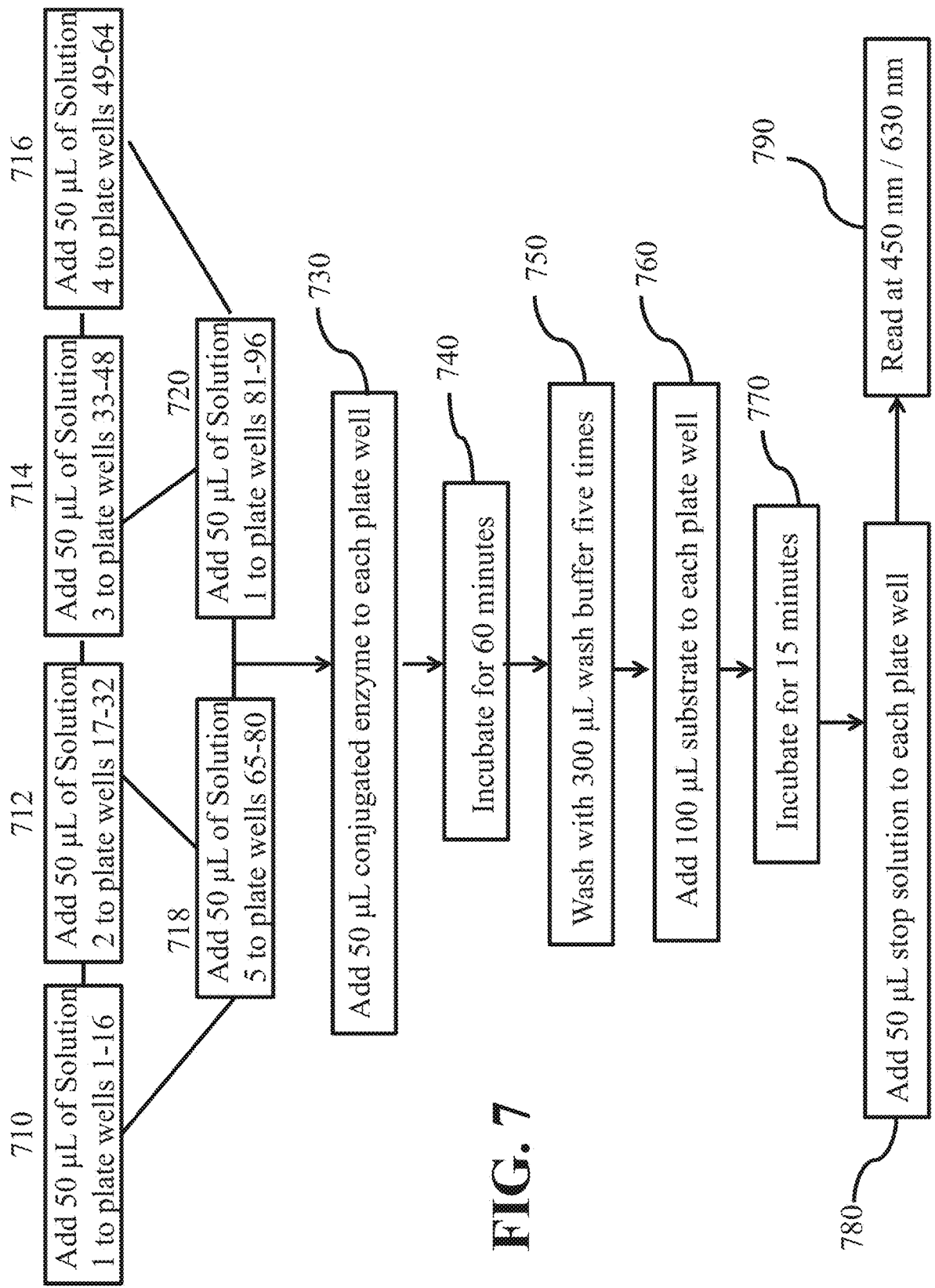
FIG. 7 is a flow chart illustrating an implementation of a method of collecting data for an ELISA instrument.

In FIG. 7, one implementation of a method of programming or use of the quality control kit with a fully automated ELISA instrument is presented in a flow chart. As noted earlier, it should be understood that times, temperatures, sources, concentrations, and/or quantities identified below for each step may be approximate and can vary depending on the desired setup of the kit.

Referring now to FIG. 7, a first step 710 of the experimental setup can include adding 50 µL of Solution 1 to plate wells 1 to 16, a second step 712 can include adding 50 µL of Solution 2 to plate wells 17 to 32, a third step 714 can include adding 50 µL of Solution 3 to plate wells 33 to 48, a fourth step 716 can include adding 50 µL of Solution 4 to plate wells 49 to 64, a fifth step 718 can include adding 50 µL of Solution 5 to plate wells 65 to 80, and a sixth step 720 can include adding 50 µL of Solution 1 to plate wells 81 to 96. In addition, a seventh step 730 can include adding 50 µL of conjugated enzyme to each plate well. Then the plate can be incubated at about 25° C. for approximately 60 minutes in an eighth step 740. In addition, in a ninth step 750, each plate well may be washed with 300 µL of wash buffer. In some implementations, there is no soaking time provided. In one implementation, the washing may be repeated such that, for example, the plate well can be washed four additional times (for a total of five times). A tenth step 760 includes adding 100 µL of substrate solution to each plate well. The plate may then be optionally incubated at about 25° C. for approximately 15 minutes in an eleventh step 770. In a twelfth step 780, 50 µL of stop solution is added to each plate well. Finally, in a thirteenth step 790, plate reader data can be read at 450 nm wavelength with a reference filter of 630 nm wavelength. Through this methodology, once the respective solutions have been placed in their specified locations for the particular instrument being evaluated, the "START" button can be clicked to initiate the experiment, and the results may be recorded. Simply for purposes of clarity, an example chart listing data results from one such experiment are presented below in Table 1. However, it should be understood that this table is provided as an example only, and values can differ across instruments and kit set up.

TABLE 1

Example results recorded following a quality control evaluation experimental run on a fully automated ELISA instrument

| | 1 | 2 | 3 | 4 | 5 | 6 | 7 | 8 | 9 | 10 | 11 | 12 |
|---|---|---|---|---|---|---|---|---|---|---|---|---|
| A | 2.11 | 2.14 | 1.21 | 1.01 | 1.61 | 1.64 | 0.53 | 0.52 | 0.53 | 0.53 | 2.12 | 2.11 |
| B | 2.13 | 2.06 | 1.21 | 1.00 | 1.59 | 1.64 | 0.43 | 0.51 | 0.53 | 0.57 | 2.11 | 2.06 |
| C | 2.07 | 2.08 | 1.18 | 1.04 | 1.66 | 1.60 | 0.55 | 0.53 | 0.52 | 0.54 | 2.11 | 2.12 |
| D | 2.09 | 2.10 | 1.12 | 1.05 | 1.62 | 1.58 | 0.52 | 0.56 | 0.55 | 0.52 | 2.08 | 2.03 |
| E | 2.21 | 2.09 | 1.11 | 1.02 | 1.67 | 1.62 | 0.52 | 0.53 | 0.50 | 0.53 | 2.09 | 2.09 |
| F | 2.01 | 2.04 | 1.04 | 1.01 | 1.57 | 1.62 | 0.50 | 0.53 | 0.52 | 0.53 | 2.13 | 2.11 |
| G | 2.02 | 2.12 | 1.05 | 1.03 | 1.63 | 1.59 | 0.54 | 0.55 | 0.51 | 0.55 | 2.10 | 2.10 |
| H | 1.99 | 2.12 | 1.06 | 1.02 | 1.64 | 1.60 | 0.54 | 0.54 | 0.50 | 0.55 | 2.12 | 2.11 |

Following the above-described procedure and data recordation, the data can be analyzed in order to provide an evaluation of the quality parameters system as disclosed herein. As discussed above, the mean, standard deviation, and coefficient of variation for each data set were read from plate wells 1 to 16, 17 to 32, 33 to 48, 49 to 64, 65 to 80, and 81 to 96, and were calculated by respectively using Formulas 1, 2, and 3 in FIGS. 6A-6C. As an example, Table 2 below presents the statistical results of sample recorded data sets. Again, it should be understood that the values presented in Table 2 are shown as an example only, and values can differ across instruments and kit set up.

TABLE 2

Example results of mean, standard deviation (SD), and coefficient of variation (CV) for each recorded data set

| | Wells 1 to 16 | Wells 17 to 32 | Wells 33 to 48 | Wells 49 to 64 | Wells 65 to 80 | Wells 81 to 96 | Total Plate |
|---|---|---|---|---|---|---|---|
| Average | 2.08 | 1.07 | 1.61 | 0.52 | 0.53 | 2.09 | — |
| Standard Deviation | 0.055 | 0.071 | 0.027 | 0.029 | 0.018 | 0.025 | — |
| Coefficient of Variation | %2.64 | %6.66 | %1.7 | %5.6 | %3.57 | %1.21 | 3.56 |

This data can then be reviewed to permit an evaluation regarding the operation of a fully automated ELISA. In some implementations, the obtained results are interpreted with reference to the COA paper as described above. One example COA is provided in TABLE 3 below.

TABLE 3

Example of acceptable ranges for the calculated test results

| | Wells 1 to 16 | Wells 17 to 32 | COA Wells 33 to 48 | Wells 49 to 64 | Wells 65 to 80 | Wells 81 to 96 |
|---|---|---|---|---|---|---|
| Acceptable Range | 1.76-2.23 | 0.91-1.09 | 0.89-1.1 | 0.46-0.54 | 0.46-0.54 | 1.58-2.45 |

Figure 8:
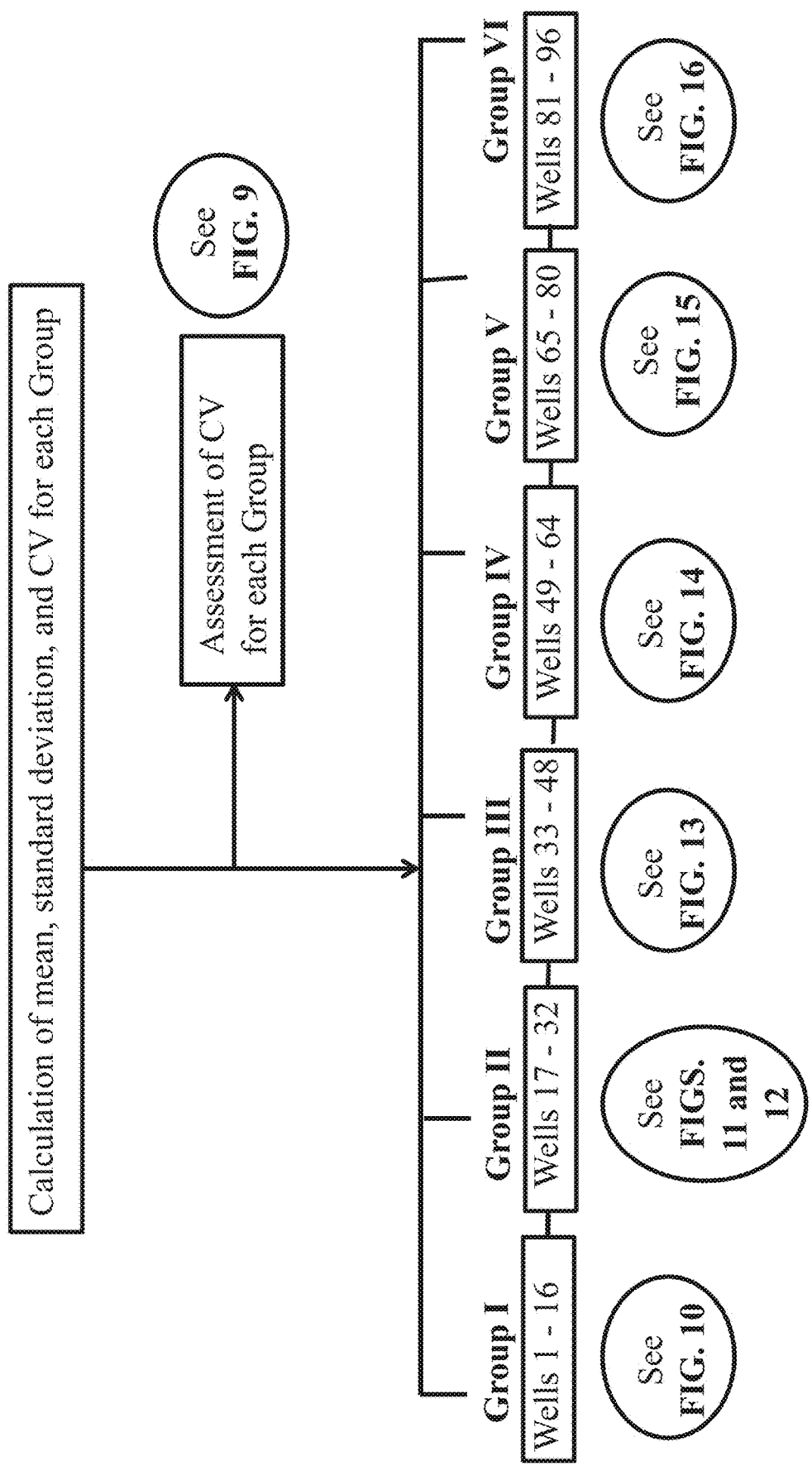
FIG. 8 is a flow chart depicting an implementation of the statistical analysis of the optical densities for the ELISA instrument.
Figure 9:
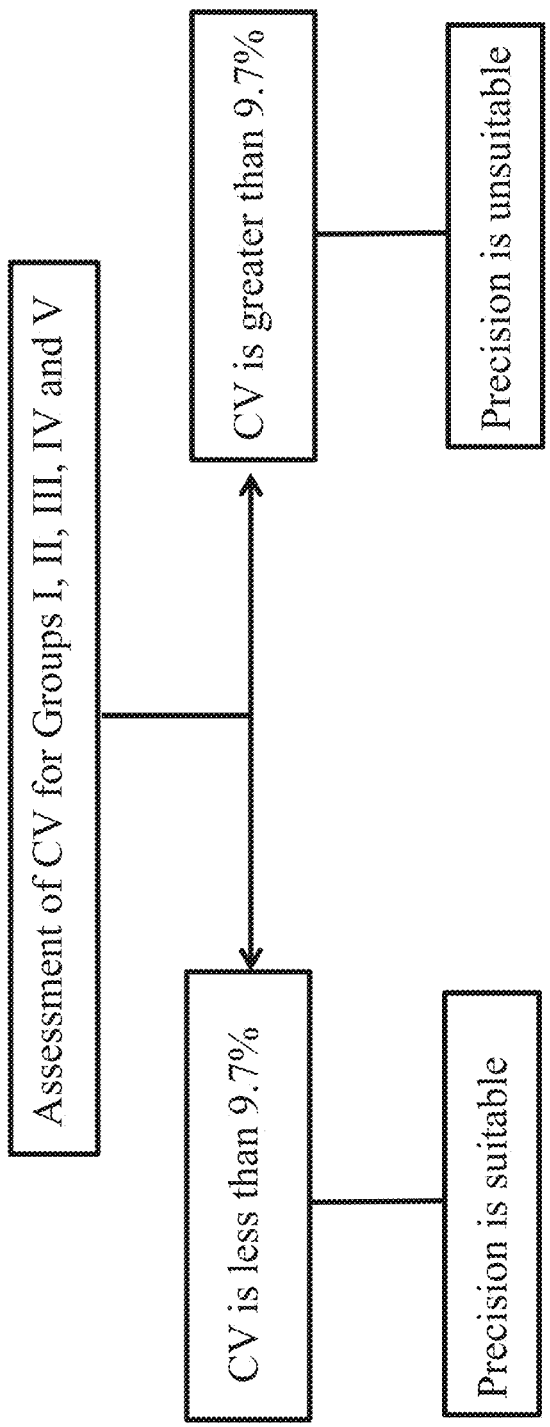
FIG. 9 is a flow chart depicting an implementation of the use of the coefficient of variation to determine the precision.
Figure 10:
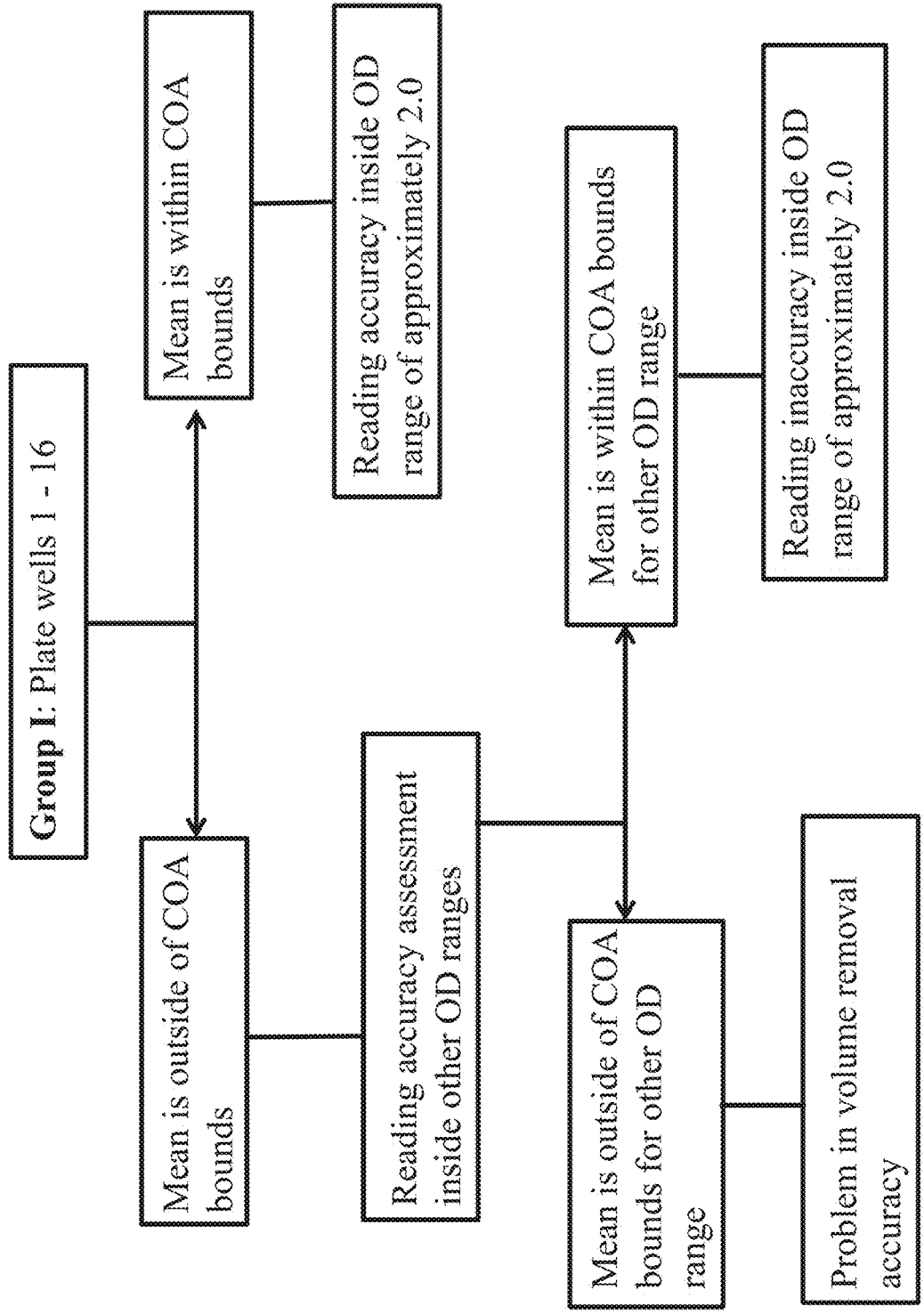
FIG. 10 is a flow chart depicting an implementation of the use of the mean to determine volume removal accuracy and reading accuracy.
Figure 11:
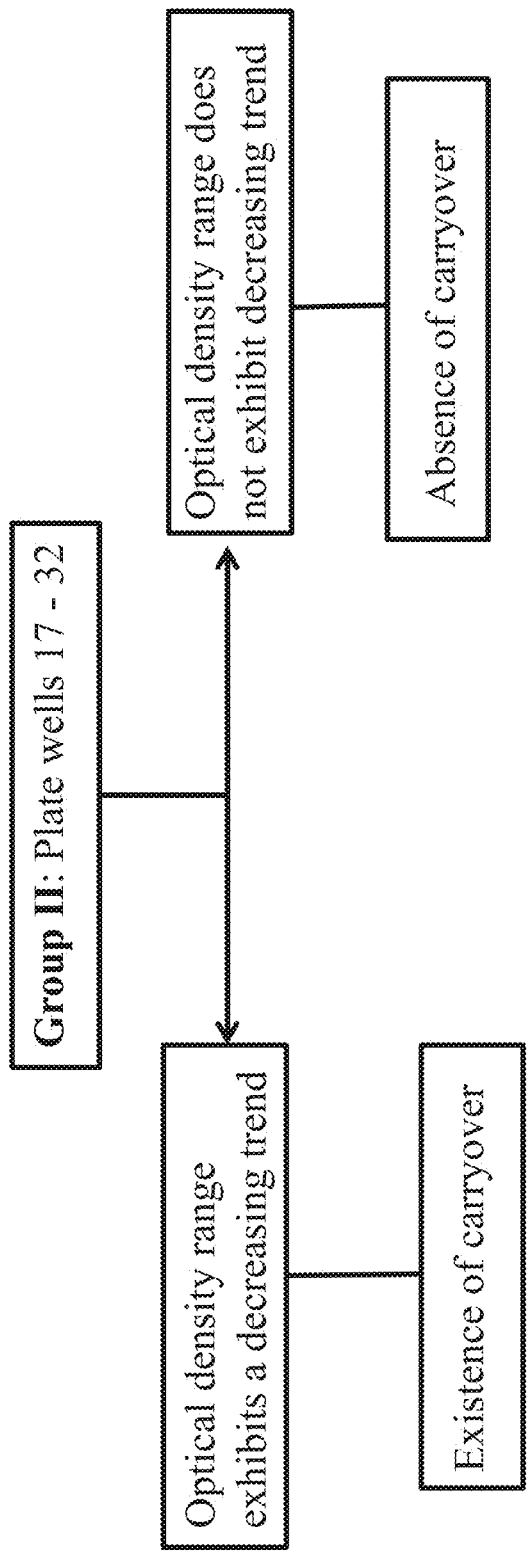
FIG. 11 is a flow chart depicting an implementation of the use of the mean to determine the absence or presence of carryover as well as reading accuracy.
Figure 12:
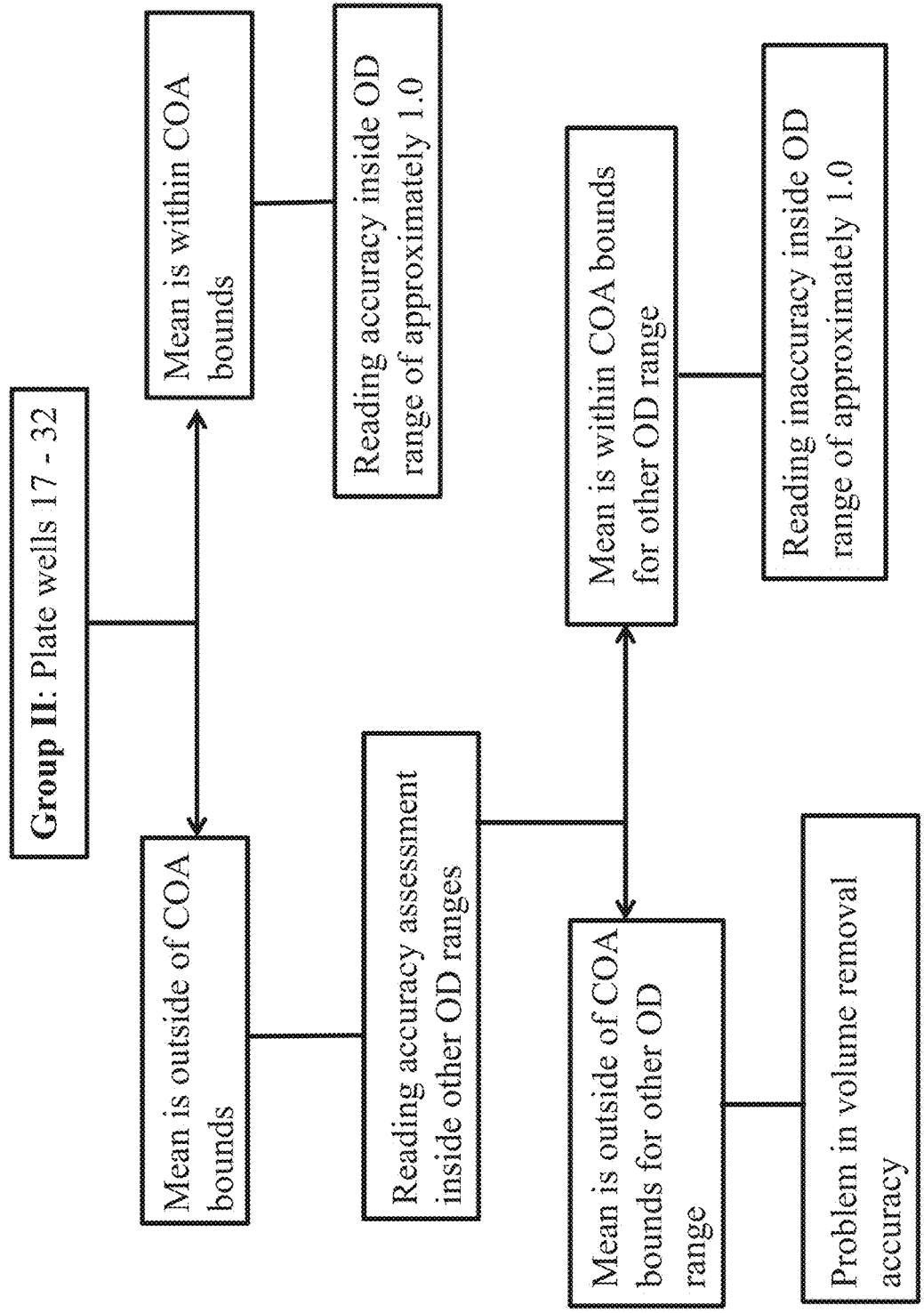
FIG. 12 is a flow chart depicting an implementation of the use of the mean to determine volume removal accuracy and reading accuracy.
Figure 13:
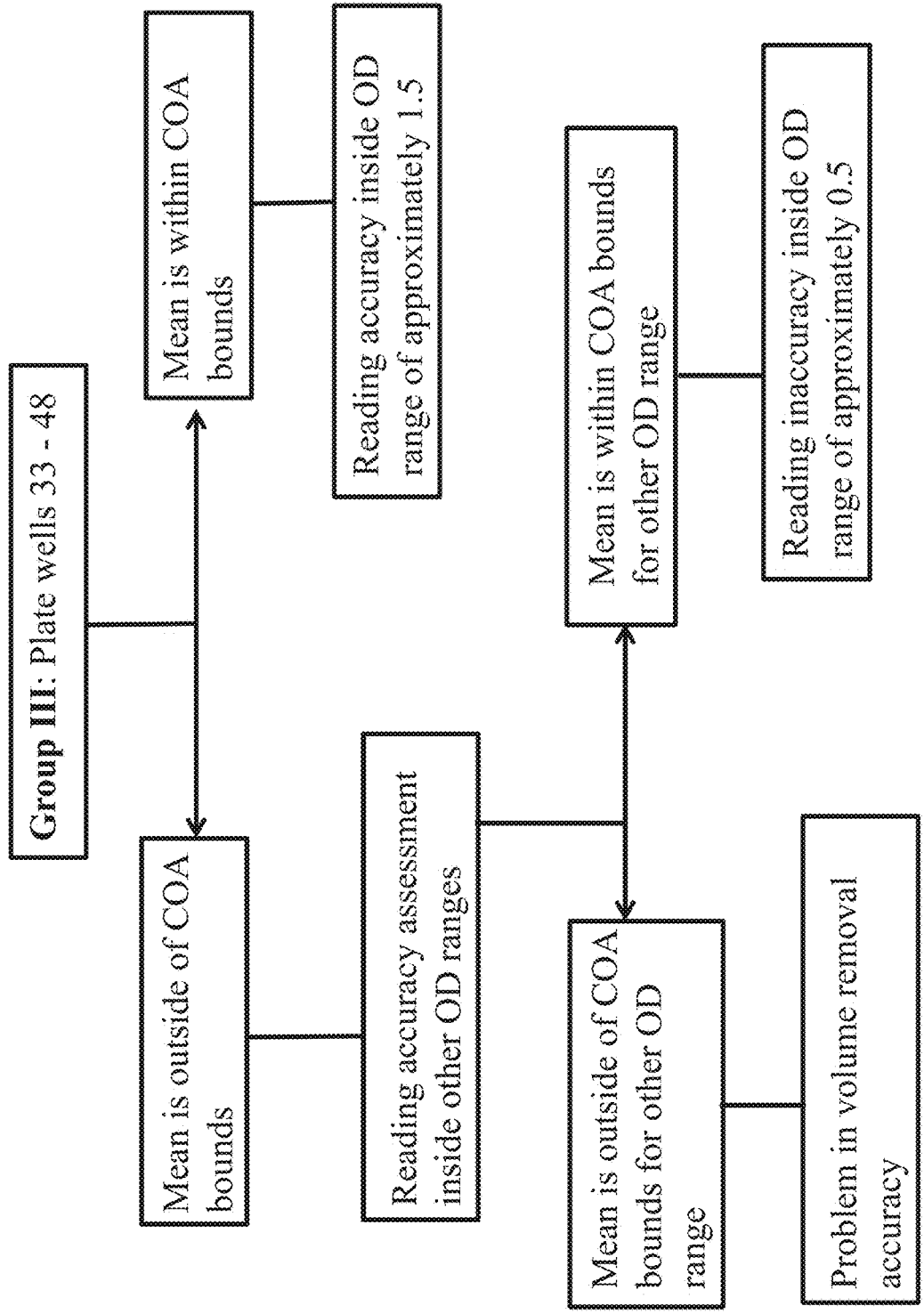
FIG. 13 is a flow chart depicting an implementation of the use of the mean to determine volume removal accuracy and reading accuracy.
Figure 14:
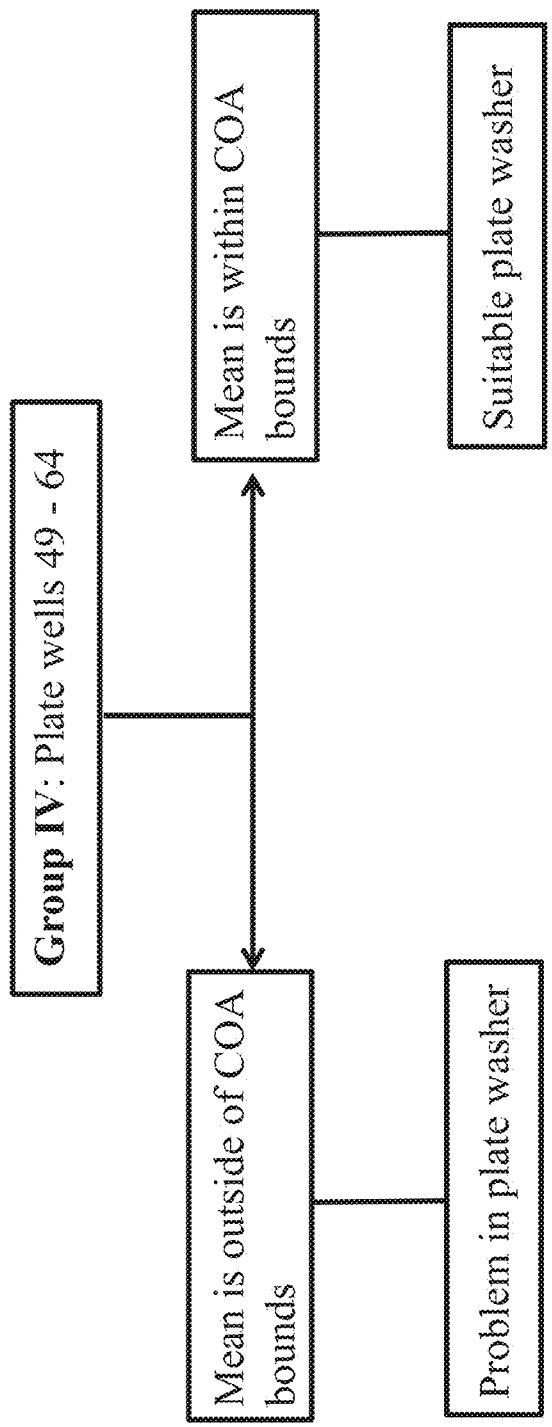
FIG. 14 is a flow chart depicting an implementation of the use of the mean to determine the absence or presence of issues with the plate washer.
Figure 15:
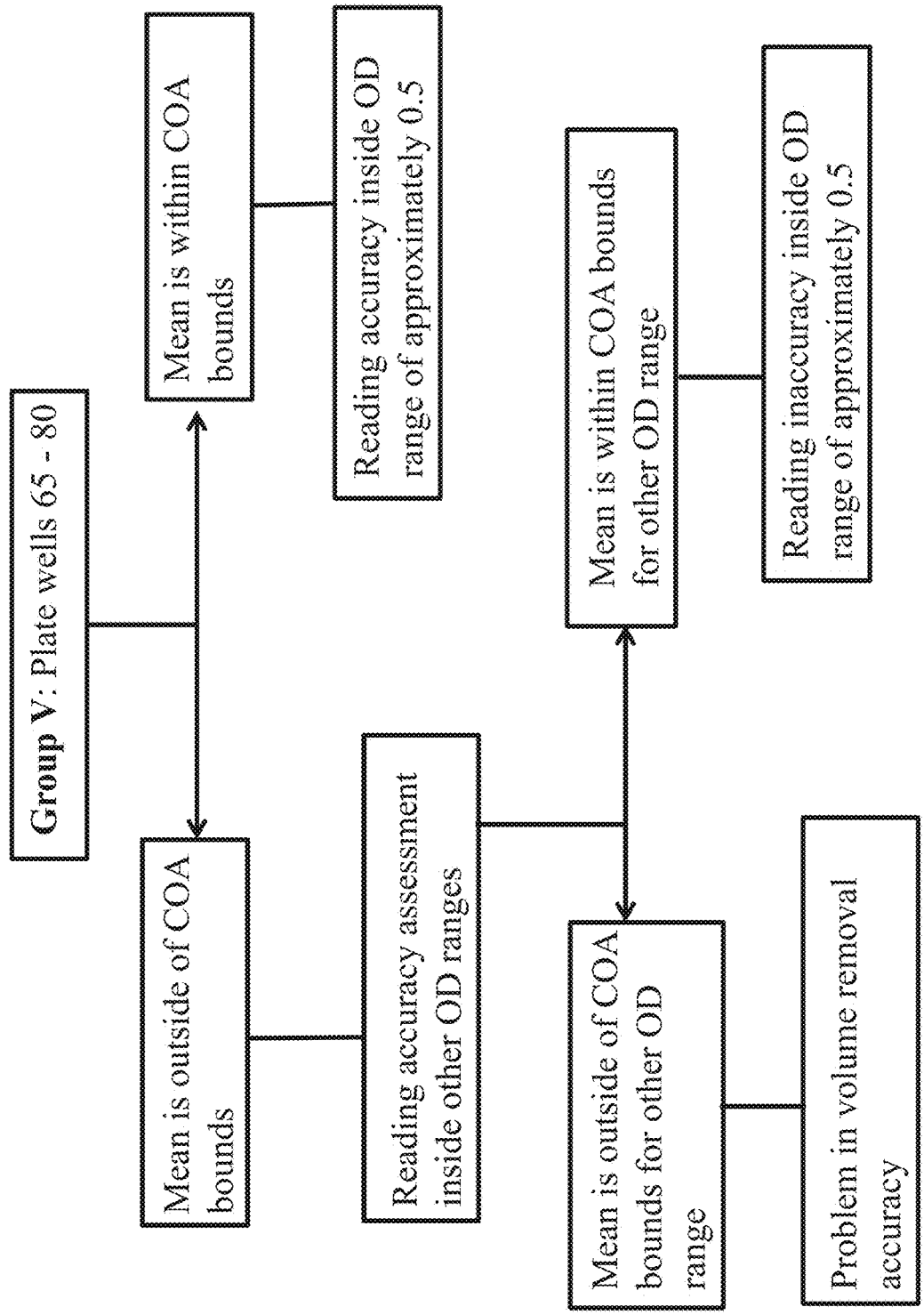
FIG. 15 is a flow chart depicting an implementation of the use of the mean to determine volume removal accuracy and reading accuracy.
Figure 16:
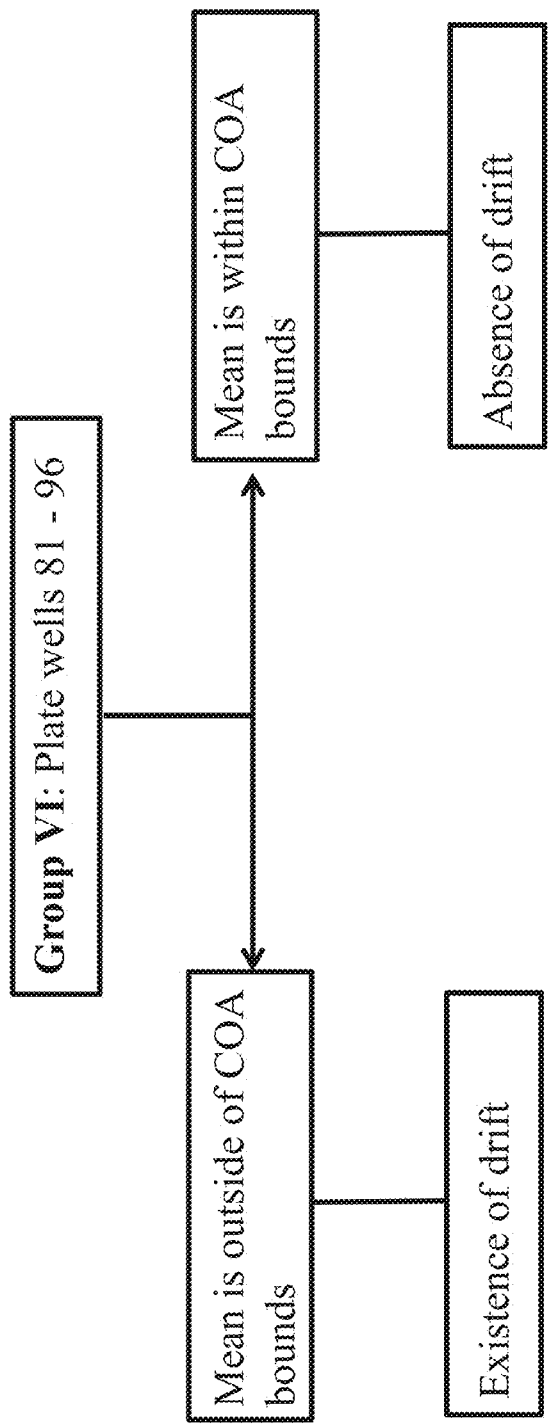
FIG. 16 is a flow chart depicting an implementation of the use of the mean to determine the absence or presence of drift.

In order to analyze the data read following the use of the quality control kit with an ELISA instrument, a series of standards or references have been developed and verified for use with the kit, herein referred to as a specification or COA paper. An implementation of the process of assessing the various quality parameters has been summarized in FIGS. 8-16. In FIG. 8, a first flow chart is shown in which the statistical analysis of the optical densities is introduced, whereby the mean, standard deviation (SD), and coefficient of variation (CV) are calculated for each well grouping. In FIG. 9, a second flow chart is used to show how the coefficient of variation of each groups' CV can be assessed for a determination of the precision of the instrument for the specified well groups. In FIG. 10, a third flow chart is used to show how the mean for Group I (Wells 1-16) can be assessed for a determination of volume removal accuracy and reading accuracy. In FIG. 11, a fourth flow chart is used to show how the mean for Group II (Wells 17-32) can also be assessed for a determination of presence or absence of carryover. In FIG. 12, a fifth flow chart is used to show how the mean for Group II (Wells 17-32) can be assessed for a determination of volume removal accuracy and reading accuracy. In FIG. 13, a sixth flow chart is used to show how the mean for Group III (Wells 33-48) can be assessed for a determination of volume removal accuracy and reading accuracy. In FIG. 14, a seventh flow chart is used to show how the mean for Group IV (Wells 49-64) can be assessed for a determination of the absence or presence of issues with the plate washer in the instrument. In FIG. 15, an eighth flow chart is used to show how the mean for Group V (Wells 65-80) can be assessed for a determination of volume removal accuracy and reading accuracy. In FIG. 16, a ninth flow chart is used to show how the mean for Group VI (Wells 81-96) can be assessed for a determination of the absence or presence of drift in the instrument.

With this context, and referring back to the data presented in Tables 1-3 above, an implementation of the developed assessment criteria for the Example case can be understood as follows: (A) If the coefficient of variation (CV) of the above-mentioned six group data sets is greater than 9.7, then the precision of instrument will not be suitable for running an experiment; (B) If the coefficient of variations of the above-mentioned six group data sets are more than 9.7, then the precision of instrument in that range of optical density (OD) will not be suitable for running an experiment; (C) If the mean of the optical density in plate wells 1 to 16 is outside the COA±3 SD bound of OD, then the accuracy of volume removal or the accuracy of the plate reader within this optical density range (approximately 2.0) will be unacceptable; (D) If the mean of the optical density in plate wells 17 to 32 is outside the COA±3 SD bound of OD, then the accuracy of volume removal or the accuracy of the plate reader within this optical density range (approximately 1.0) will be unacceptable; (E) If the mean of the optical density in plate wells 33 to 48 is outside the COA±3SD bound of OD, then the accuracy of volume removal or the accuracy of the plate reader within this optical density range (approximately 1.5) will be unacceptable; (F) If the mean of the optical density in plate wells 49 to 64 is outside the COA±3SD bound of OD, then the accuracy of the plate washer will not be suitable; (G) If the mean of the optical density in plate wells 65 to 80 is outside the COA±3SD bound of OD, then the accuracy of volume removal or the accuracy of the plate reader within this optical density range (approximately 0.5) will be unacceptable; (H.1) If there is a problem in the accuracy of volume removal, then there will be a problem in the results of plate wells 1 to 48, but the problem will not be observed in the results of plate wells 65 to 80, (H.2) If there is a problem in the accuracy of the plate reader within each individual optical density range, then there will only be a problem in the results of plate wells within that specific optical density range, and (H.3) If there is a problem in the accuracy of the plate reader in all optical density ranges, then the problem will also be observed in plate wells 65 to 80; (I) If the results of optical density in plate wells 17 to 32 indicate higher magnitudes in the beginning plate wells, but approach the actual results in a direction gradually moving towards the ending plate wells, then a carryover will exist; and (J) If the mean of the data sets in plate wells 81 to 96 is more than 10% of the mean of the data sets in plate wells 1 to 16, then a drift will exist.

Thus, applying the above standard, the collected data and calculated statistical values of the Example case can be evaluated. In this specific example, it can be seen that since the coefficient of variations of all data sets (the entire plate) are lower than 9.7, the precision of the instrument is acceptable. Furthermore, because the optical density (OD) means of all data sets are within the calculated bound of COA, the accuracy and the linearity of plate reader is acceptable. Similarly, since the OD mean of plate wells 49 to 64 is within the calculated bound of COA, the accuracy of the plate washer is suitable. In addition, because the OD mean of plate wells 81 to 96 is within the calculated bound of COA, the instrument has no indication of a drift problem. However, because the OD results indicates a higher magnitude in the beginning plate wells (17 to 32) and a lower magnitude in a direction approaching the ending plate wells, the instrument has a carryover problem.

Accordingly, in different implementations, the precision of all types of fully automated open ELISA instruments can be assessed by repeating the disclosed process or experiment on various sample concentrations of an analyte of interest, which can permit the analysis of the precision is evaluated over a number of concentrations. In addition, in some implementations, the accuracy and the linearity of the plate reader in fully automated open ELISA instruments can be assessed by running the experiment on samples with a specified optical density (OD) range (specified analyte concentration) within a lower and an upper bound of the OD range (low to high analyte concentration). Furthermore, in other implementations, the accuracy of the volume removal in fully automated open ELISA instruments can be assessed by analyzing final ODs within their predetermined ranges. Similarly, the use of this kit allows a determination of the accuracy of the plate washer in fully automated open ELISA instruments by washing plate wells containing concentrated dye reagents. In one implementation, the presence of a carryover in any types of fully automated open ELISA instruments can be determined by running the experiment first on samples with highly concentrated analytes followed by samples with lower concentrated analytes. In addition, the presence of a drift in a fully automated open ELISA instruments can be determined by running the experiment on a sample across a few hours. The algorithms and standards disclosed herein can be standardized and facilitate the detection of quality issues in any fully automated ELISA instrument.

With this approach to quality control, assessing all quality control parameters involved in using a fully automated ELISA instrument simply and effectively has been made possible. Through the use of a quality control kit as described herein, critical quality parameters, including instrument precision, volume removal accuracy, plate reader accuracy, plate washer quality, drift absence, and carryover absence, can be reliably assessed.

Furthermore, beyond the direct benefit of ascertaining these parameters of a fully automated ELISA instrument, the disclosed implementations offer many additional advantages. For example, the kits and methods described herein offer the possibility of using the quality control kit across a wide range of fully automated ELISA instruments and models, manufactured by different companies worldwide, without limitation. In addition, the use of this kit can permit the assessment of all quality control parameters of a fully automated ELISA instrument all at once (for example, in a single work shift), and often in less than two hours. The costs associated with the kit are relatively low, and the simplicity in its application can allow many different personnel to perform the assessment with minimal additional training. Other benefits include the ability to diagnose precisely a problem(s) in an instrument by a single experiment or process, and a high degree of reliability of results obtained from running the experiment. Furthermore, this method can offer the possibility of inspecting the quality of a fully automated ELISA instrument prior to a clinical laboratory purchase, thereby preserving financial resources, particularly in countries where the ELISA apparatus must be imported. In addition, the disclosed kit can be easily exported or shipped for use in laboratories worldwide.

While various embodiments have been described, the description is intended to be exemplary, rather than limiting, and it is understood that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus the following claims are hereby incorporated into the Detailed Description, with each claim standing on its own as a separately claimed subject matter.

What is claimed is:

1. A method for evaluating quality control parameters of an automated ELISA instrument, the method comprising:
   preparing a micro plate that includes at least 96 plate wells;
   adding a first amount of a first solution to plate wells 1 to 16 of the at least 96 plate wells;
   adding a second amount of a second solution to plate wells 17 to 32 of the at least 96 plate wells;
   adding a third amount of a third solution to plate wells 33 to 48 of the at least 96 plate wells;
   adding a fourth amount of a fourth solution to plate wells 49 to 64 of the at least 96 plate wells;
   adding a fifth amount of a fifth solution to plate wells 65 to 80 of the at least 96 plate wells;
   adding the first amount of the first solution to plate wells 81 to 96 of the at least 96 plate wells;
   adding a sixth amount of conjugated enzyme to each of the 96 plate wells;
   washing each of the at least 96 plate wells with a wash buffer;
   preparing and adding a seventh amount of substrate solution to each of the at least 96 plate wells;
   preparing and adding an eighth amount of stop solution to each of the at least 96 plate wells;
   obtaining a first reading of data from plate wells 1 to 16 of the automated ELISA instrument, the data being related to optical density of plate wells 1 to 16;
   calculating a first mean for the data of the plate wells 1 to 16;
   comparing the first mean with a first acceptable range provided in a certificate of analysis (COA) paper for plate wells 1 to 16, thereby determining whether the first readings for the automated ELISA instrument are accurate.

2. The method of claim 1, wherein preparing the micro plate includes pre-coating a bottom surface of the plate wells with anti-Human Thyroid Stimulating Hormone (TSH) antibody.

3. The method of claim 1, further comprising drying the plate wells.

4. The method of claim 1, wherein preparing the substrate solution includes adding 5 μL $H_2O_2$ and 10 μL tetra-methylbenzidine (TMB) to 100 mL acetate buffer.

5. The method of claim 1, wherein preparing the stop solution includes adding 1 mL tartrazine to 11 mL sulfuric acid.

6. The method of claim 1, wherein
   the first amount comprises 50 μL and the first solution comprises TSH,
   the second amount comprises 50 μL and the second solution comprises TSH,
   the third amount comprises 50 μL and the third solution comprises TSH,
   the fourth amount comprises 50 μL and the fourth solution comprises concentrated yellow dye reagent, and
   the fifth amount comprises 50 μL and the fifth solution comprises distilled water.

7. The method of claim 6, further comprising preparing the first solution by dissolving approximately 20 mg TSH powder in approximately 5 mL delipidated serum.

8. The method of claim 7, further comprising:
   preparing the second solution by dissolving approximately 13 mg TSH powder in approximately 5 mL delipidated serum, and
   preparing the third solution by dissolving approximately 28 mg TSH powder in approximately 5 mL delipidated serum.

9. The method of claim 1, further comprising:
   obtaining a second reading of data from plate wells 17 to 32 of the automated ELISA instrument;
   calculating a second mean for the data of the second reading for the plate wells 17 to 32; and
   comparing the second mean with a second acceptable mean range provided in the COA paper for plate wells 17 to 32, thereby determining whether readings and volume removal for the automated ELISA instrument are accurate.

10. The method of claim 9, wherein adding conjugated enzyme to each of the 96 plate wells includes adding 50 μL of horseradish peroxidase (HRP) conjugated antibody to each of the 96 plate wells.

11. The method of claim 1, further comprising:
    obtaining a second reading of data from plate wells 33 to 48 of the automated ELISA instrument;
    calculating a second mean for the data of the second reading for the plate wells 33 to 48; and
    comparing the second mean with a second acceptable mean range provided in the COA paper for plate wells 33 to 48, thereby determining whether readings and volume removal for the automated ELISA instrument are accurate.

12. The method of claim 1, further comprising:
    obtaining a second reading of data from plate wells 49 to 64 of the automated ELISA instrument;
    calculating a second mean for the data of the second reading for the plate wells 49 to 64; and
    comparing the second mean with a second acceptable mean range provided in the COA paper for plate wells 49 to 64, thereby determining whether a plate washer of the automated ELISA instrument is functioning within normal operating parameters.

13. The method of claim 1, further comprising:
obtaining a second reading of data from plate wells 65 to 80 of the automated ELISA instrument;
calculating a second mean for the data of the second reading for the plate wells 65 to 80; and
comparing the second mean with a second acceptable mean range provided in the COA paper for plate wells 65 to 80, thereby determining whether readings and volume removal for the automated ELISA instrument are acceptable.

14. The method of claim 1, further comprising:
obtaining a second reading of data from plate wells 81 to 96 of the automated ELISA instrument;
calculating a second mean for the data of the second reading for the plate wells 81 to 96; and
comparing the second mean with a second acceptable mean range provided in the COA paper for plate wells 81 to 96, thereby determining whether there is drift in the automated ELISA instrument.

15. The method of claim 1, further comprising:
calculating a first coefficient of variation (CV) for the data of the first reading; and
comparing the first coefficient of variation with a first acceptable CV cutoff provided in the COA paper for plate wells 1 to 16, thereby determining a precision of the automated ELISA instrument.

16. The method of claim 15, wherein the precision of the automated ELISA instrument is unsuitable if the first coefficient of variation is greater than 9.7%.

17. The method of claim 9, further comprising comparing the second mean with the second acceptable range provided in the COA paper for plate wells 17 to 32, thereby determining whether there is carryover in the automated ELISA instrument.

18. The method of claim 1, further comprising:
obtaining a second reading from plate wells 17 to 32, a third reading from plate wells 33-48, a fourth reading from plate wells 49-64, a fifth reading from plate wells 65 to 80, and a sixth reading from plate wells 81-96;
calculating a second mean for the data of the second reading,
calculating a third mean for the data of the third reading,
calculating a fourth mean for the data of the fourth reading,
calculating a fifth mean for the data of the fifth reading, and
calculating a sixth mean for the data of the sixth reading;
comparing the second mean with a second acceptable mean range provided in the COA paper for plate wells 17 to 32; and
determining there is carryover in the automated ELISA instrument if the second mean is higher than the second acceptable mean range and each of the readings for plate wells 33 to 96 approach values provided in the COA paper.

19. The method of claim 1, further comprising:
obtaining a second reading of data from plate wells 81 to 96;
calculating a second mean for the data of the second reading; and
determining there is drift in the automated ELISA instrument if the second mean is more than 10% of the first mean.

* * * * *